United States Patent
Fraiman

(10) Patent No.: US 7,296,997 B2
(45) Date of Patent: Nov. 20, 2007

(54) APPARATUS FOR SIMULATING INTERDENTAL PAPILLA

(76) Inventor: Howard Fraiman, 20 E. Princeton Rd., Bala Cynwyd, PA (US) 19004

( * ) Notice: Subject to any disclaimer, the term of this patent is extended or adjusted under 35 U.S.C. 154(b) by 0 days.

(21) Appl. No.: 11/076,440

(22) Filed: Mar. 9, 2005

(65) Prior Publication Data

US 2005/0282113 A1 Dec. 22, 2005

Related U.S. Application Data

(60) Provisional application No. 60/552,651, filed on Mar. 12, 2004.

(51) Int. Cl.
*A61C 8/00* (2006.01)
(52) U.S. Cl. .................................................... 433/173
(58) Field of Classification Search ................ 433/173, 433/141; 132/321, 329
See application file for complete search history.

(56) References Cited

U.S. PATENT DOCUMENTS

| | | | | | |
|---|---|---|---|---|---|
| 2,552,134 | A | * | 5/1951 | Berliner | 433/143 |
| 2,760,628 | A | * | 8/1956 | Briggs | 206/104 |
| 3,890,714 | A | * | 6/1975 | Gores | 433/149 |
| 5,499,918 | A | * | 3/1996 | Morgan et al. | 433/173 |
| D379,250 | S | * | 5/1997 | Brewer | D28/65 |
| 6,019,604 | A | * | 2/2000 | Gougeon | 433/168.1 |
| 6,213,774 | B1 | * | 4/2001 | Lazarof | 433/173 |
| 6,220,258 | B1 | * | 4/2001 | Briggs et al. | 132/329 |

* cited by examiner

*Primary Examiner*—Ralph A. Lewis
(74) *Attorney, Agent, or Firm*—Charles N. Quinn, Esq.

(57) ABSTRACT

An apparatus for simulating interdental papilla having a support for interdental gingival tissue and an attachment for securing the support to an interimplant bone.

18 Claims, 4 Drawing Sheets

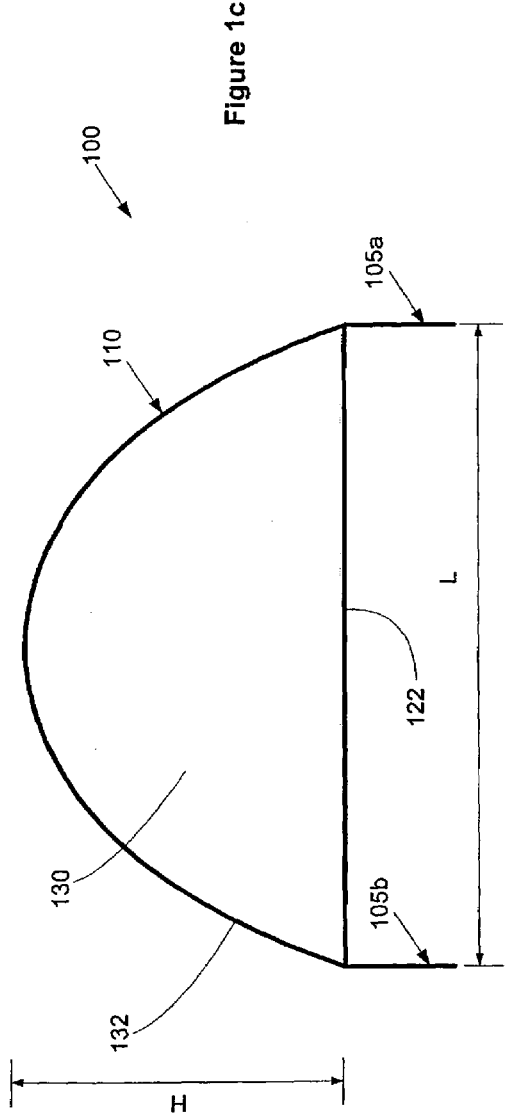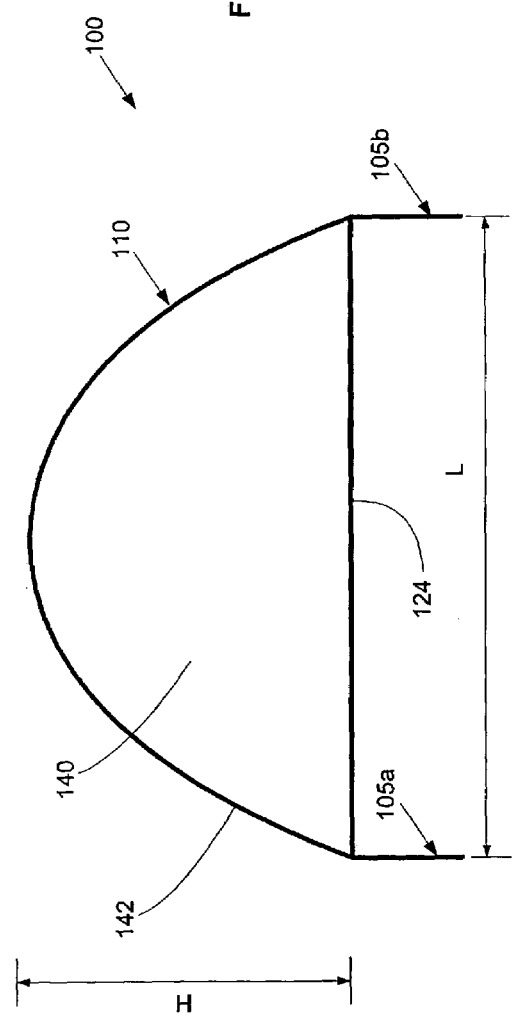

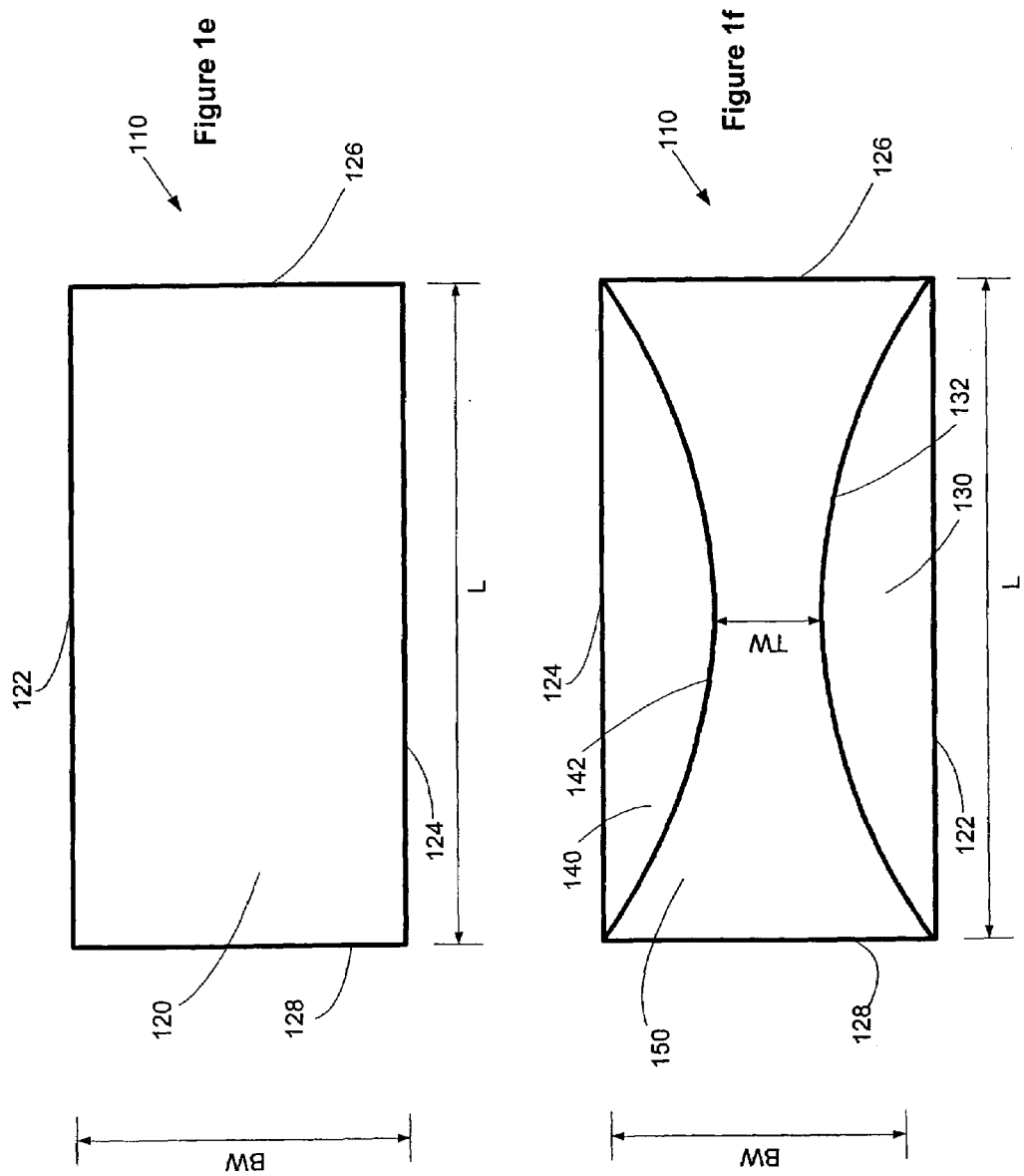

APPARATUS FOR SIMULATING INTERDENTAL PAPILLA

CROSS-REFERENCE TO RELATED PATENT APPLICATION

This patent application claims the benefit under 35 U.S.C. 119 and 120 of the filing date and priority of provisional U.S. patent application Ser. No. 60/552,651 filed Mar. 12, 2004.

BACKGROUND OF THE INVENTION

1. Field of Invention

The invention disclosed herein relates generally to an apparatus for simulating interdental papilla between dental implants. More specifically, preferred embodiments of the disclosed invention relate to a papilla tack for supporting gingival tissues between osseointegrated dental implants.

2. Description of the Prior Art

It is known in the art to use dental implants to replace human teeth. Under circumstances known in the art, there are cases when multiple dental implants are used to replace multiple human teeth. The dental implants are anchored into the bone of the jaw and are referenced as osseointegrated dental implants. A problem occurs when multiple dental implants are adjacent one another, replacing adjacent teeth. Healthy teeth are usually surrounded by healthy gingival tissues appearing papilla-like to an onlooker. However, in the case of adjacent dental implants, the interdental gingival tissue is flat, leaving a visible embrasure between the teeth. This embrasure is not aesthetically pleasing for onlookers, and the open embrasure is a give away that dental implants are being utilized in place of real teeth. This is quite embarrassing for individuals having dental implants and presents additional problems as well (e.g. food can get stuck in the embrasure). What is needed is an apparatus for simulating interdental papilla to increase the aesthetic appeal of the interdental region and to minimize any embarrassment and/or discomfort that might be felt by the individual having the dental implants.

SUMMARY OF THE INVENTION

Disclosed herein is an apparatus for simulating interdental papilla. The preferred apparatus preferably comprises a base, a front stabilizing pin and a rear stabilizing pin. The base is preferably sized to be positioned between osseointegrated dental implants within an interdental embrasure and beneath at least a portion of the interdental gingival tissue. In some aspects, the apparatus for simulating interdental papilla comprises a papilla tack.

The base preferably comprises a bottom surface, a left side surface, a right side surface and a top surface. The bottom surface is preferably rectangular and preferably comprises a left bottom edge, a right bottom edge, a front bottom edge and a rear bottom edge. The enclosed surface area of the left side surface is preferably defined by the left bottom edge and a left curved edge connecting the endpoints of the left bottom edge. The left side interior angle formed between the left side surface and the bottom surface is preferably greater than about sixty degrees and less than about ninety degrees.

The enclosed surface area of the right side surface is preferably defined by the right bottom edge and a right curved edge connecting the endpoints of the right bottom edge. A right side interior angle is preferably formed between the right side surface and the bottom surface that is about equal to the left side angle. The top surface is preferably defined by the front bottom edge, the rear bottom edge, the left curved edge and the right curved edge.

The base is preferably characterized by dimensions comprising a top width, a bottom width, a length and a height. The top width, preferably measured at a highest point of the base, is preferably about one half millimeter. The bottom width is preferably about three times the top width, and more preferably about one and one half millimeters. The length is preferably about six times the top width, and more preferably about three millimeters. The height is preferably about three times the top width, and more preferably about one and one half millimeters.

The rear stabilizing pin and the front stabilizing pin preferably extend downwardly from the base for securing the base to an interimplant bone. Each of the front and rear stabilizing pins preferably comprise a substantially triangular plane joining with the bottom surface at an edge of the substantially triangular plane. Each of the front and rear stabilizing pins preferably have hardness and sharpness of a magnitude such that each of the front and rear stabilizing pins may be anchored into the interimplant bone.

These and other features and objects of the invention will be more fully understood from the following detailed description of the preferred embodiments, which should be read in light of the accompanying drawings.

BRIEF DESCRIPTION OF THE DRAWINGS

The accompanying drawings, which form a part of the specification, illustrate the invention.

FIG. 1b is a rear view showing the preferred embodiment of the papilla tack shown in FIG. 1a.

FIG. 1c is a left side view showing the preferred embodiment of the papilla tack shown in FIG. 1a.

FIG. 1d is a right side view showing the preferred embodiment of the papilla tack shown in FIG. 1a.

FIG. 1e is a bottom view showing a preferred embodiment of a base of the papilla tack shown in FIG. 1a.

FIG. 1f is a top view showing the preferred embodiment of the base shown in FIG. 1e.

FIG. 2b is a front view showing the preferred embodiment of the papilla tack shown in FIG. 1a positioned within the embrasure shown in FIG. 2a.

Figure 1B:
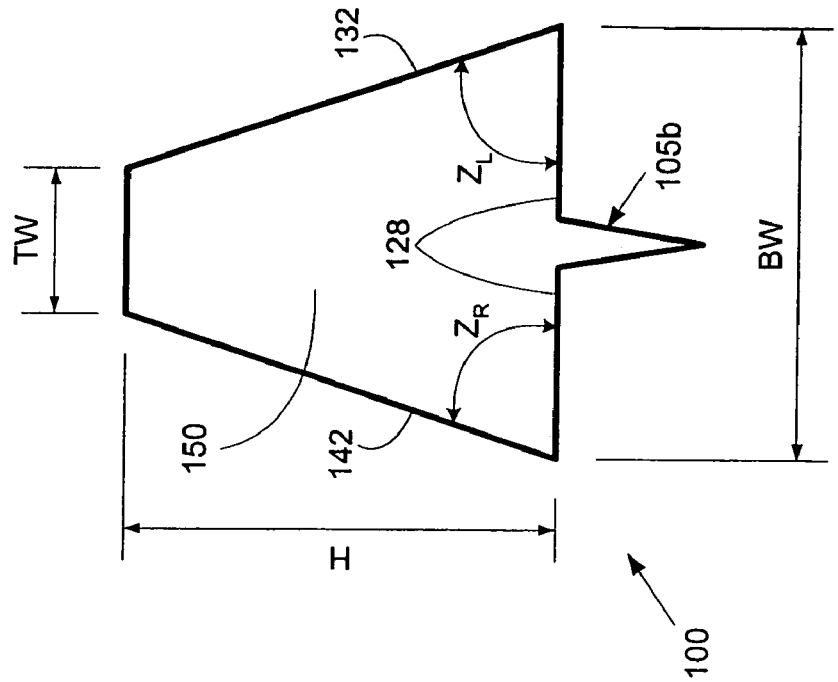

DESCRIPTION OF THE PREFERRED EMBODIMENTS AND BEST MODE KNOWN FOR PRACTICING THE INVENTION

In describing a preferred embodiment of the invention illustrated in the drawings, specific terminology will be used for the sake of clarity. However, the invention is not intended to be limited to the specific terms so selected, and it is to be understood that each specific term includes all technical equivalents which operate in a similar manner to accomplish a similar purpose.

With principal reference to FIGS. 1a through 1f, an embodiment of a papilla tack is shown and designated generally 100. Papilla tack 100 preferably comprises base 110 and at least one stabilizing pin, preferably a front stabilizing pin 105a and a rear stabilizing pin 105b. Base 110 comprises a preferably bottom surface 120 a left side surface 130, a right side surface 140 and a top surface 150. With principal reference to FIG. 1e, the enclosed surface area of bottom surface 120 is preferably defined by a left bottom edge 122, a right bottom edge 124, a front bottom edge 126 and a rear bottom edge 128. Bottom surface 120 is preferably planar.

With principal reference to FIG. 1c, the enclosed surface area of left side surface 130 is preferably defined by left bottom edge 122 and a left curved edge 132 connecting the endpoints of left bottom edge 122. A left side interior angle $Z_L$ is formed between left side surface 130 and bottom surface 120. Left side interior angle $Z_L$ is preferably greater than about sixty degrees and preferably less than about ninety degrees.

With principal reference to FIG. 1e, the enclosed surface area of right side surface 140 is preferably defined by right bottom edge 124 and a right curved edge 142 connecting the endpoints of right bottom edge 124. A right side interior angle $Z_R$ is formed between right side surface 140 and bottom surface 120. Right side interior angle $Z_R$ is preferably greater than about sixty degrees and preferably less than about ninety degrees. In preferred embodiments, left side interior angle $Z_L$ is about equal to right side interior angle $Z_R$.

Figure 1A:
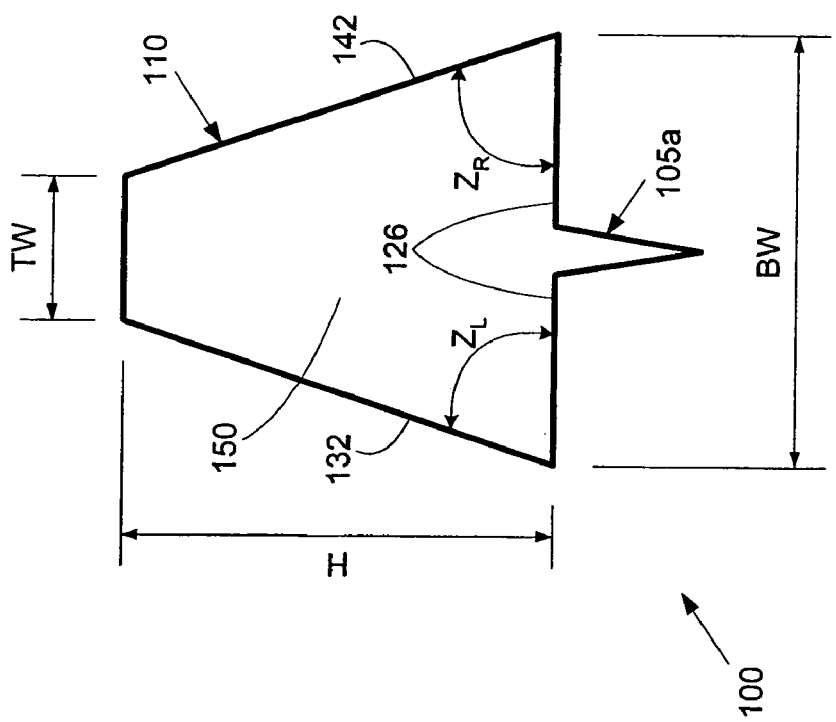
FIG. 1a is a front view showing a preferred embodiment of a papilla tack.

With principal reference to FIG. 1f, the enclosed area of top surface 150 is preferably defined by front bottom edge 126, rear bottom edge 128, left curved edge 132 and right curved edge 142. As shown, top surface 150 curves along with left curved edge 132 and right curved edge 142, preferably reaching height H approximately half way along length L. As shown in FIGS. 1a through 1b, preferred embodiments of base 110 appears substantially trapezoidal from front and rear views.

Base 110 is preferably sized to be positioned between osseointegrated dental implants, within an interdental embrasure and beneath at least a portion of the interdental gingival tissue. In addition to length L and height H, the dimensions of base 110 preferably also includes a top width TW measured at the highest point of base 110. Top width TW is preferably measured across top surface 150 half way along length L. Furthermore, the dimensions of base 110 preferably include a bottom width BW, which is about three times top width TW. In preferred embodiments, length L is about six times top width TW, height H is about three times top width TW and bottom width BW is about three times top width TW. More preferably, top width TW is about one half millimeter, bottom width BW is about one and one half millimeters, length L is about three millimeters and height H is about one and one half millimeters.

Base 110 is the preferred embodiment of support means for supporting interdental gingival tissue. However, a base of any suitable shape and/or other dental scaffolding can be used to support the interdental tissue. Any suitable support means can be utilized so long as it supports interdental gingival tissue in a manner such as to simulate the appearance of an interdental papilla.

Continuing with reference to FIGS. 1a through 1d, base 110 preferably includes front stabilizing pin 105a and rear stabilizing pin 105b, both preferably extending downward from bottom surface 120. Each of front stabilizing pin 105a and rear stabilizing pin 105b preferably define an angle of ninety degrees with respect to bottom surface 120. In preferred embodiments, each of front stabilizing pin 105a and rear stabilizing pin 105b comprise a substantially triangular plane sharing an edge of the triangle with bottom surface 120. Furthermore, each of front stabilizing pin 105a and rear stabilizing pin 105b have a hardness and sharpness of a magnitude such that each is adapted to be anchored into the interimplant bone.

At least one stabilizing pin 105 is a preferred means for securing the supporting means (the base, other means, etc.) to an interimplant bone. Stabilizing pins 105 of any suitable shape can be utilized. Any suitable securing means (glue, clamp, etc.) can be utilized so long as it secures the supporting means in a manner such as to simulate the appearance of an interdental papilla.

Figure 2A:
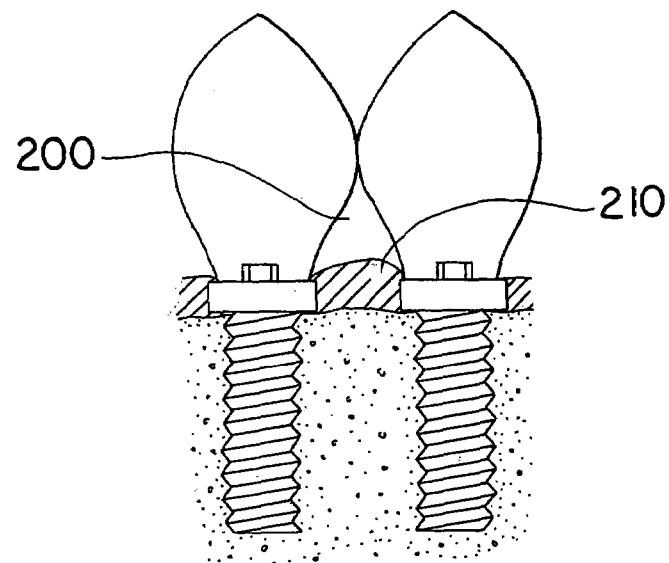
FIG. 2a is a front view showing an embrasure between osseointegrated interdental implants.

With principal reference to FIGS. 2a, a pair of osseointegrated dental implants are shown with an open embrasure 200 between the dental implants. The gingival tissue 210 is located between the dental implants. However, absent implantation of papilla tack 100, interdental gingival tissue 210 is typically unraised and fails to maintain a papilla-like appearance.

Figure 2B:
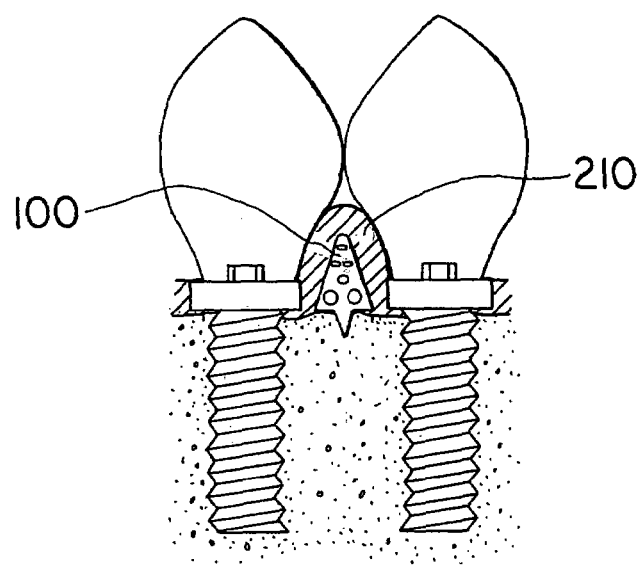

With principal reference to FIG. 2b, a pair of osseointegrated dental implants are shown with an embodiment of papilla tack 100 implanted there between. Using stabilizing pins 105 or other securing means, papilla tack 100 is anchored into the bone between the dental implants either at the time of dental implant placement or in a subsequent surgical intervention. Papilla tack is preferably implanted beneath the interdental gingival tissues 210, forcing interdental gingival tissue 210 outward.

Papilla tack 100 provides support for interdental gingival tissue 210, such support not otherwise being present. This provides an appearance between the two dental implants of an interdental embrasure 200 that is filled with normal gingival tissue. Base 110 (and/or other support means) provides a scaffolding for interimplant gingival tissue 210 over a prolonged period of time, while stabilizing pins 105 (and/or other securing means) anchor the base and/or other support means to the implant bone.

Although there has been hereinabove described an apparatus for simulating interdental papilla, in accordance with the present invention, for the purposes of illustrating the manner in which the invention may be used to advantage it should be appreciated that the invention is not limited thereto. Accordingly, any and all modifications, variations, or equivalent arrangements which may occur to one skilled in the art should be considered to be within the scope of the present invention as defined in the appended claims.

What is claimed is:

1. An apparatus for simulating interdental papilla, comprising:
   means in the form of a generally trapezoidal polyhedron for supporting interdental gingival tissue; and
   a pair of pin means extending outwardly from a single surface of said polyhedron for securing the means for supporting interdental gingival tissue to an interimplant bone.

2. The apparatus of claim 1, wherein the means for supporting interdental gingival tissue comprises a rectangular base and the pin means extends outwardly therefrom parallel one with another.

3. The apparatus of claim 2, wherein the means for supporting interdental gingival tissue is sized to be positioned within an interdental embrasure.

4. The apparatus of claim 3, wherein the means for supporting interdental gingival tissue is sized to be positioned beneath at least a portion of the interdental gingival tissue.

5. The apparatus of claim 4, wherein the base is planar and sized to be positioned between osseointegrated dental implants.

6. The apparatus of claim 5, wherein at least one pin extends perpendicularly outwardly from the planar base of the support means.

7. The apparatus of claim 6, wherein the pair of pin means stabilizing pin comprise a front stabilizing pin and a rear stabilizing pin, both of which extend outwardly perpendicularly from the planar base of the support means.

8. Apparatus of claim 6 wherein at least one stabilizing pin has a hardness and sharpness sufficient for the pin to be anchored into interimplant bone.

9. Apparatus for simulating interdental papilla, comprising:
   support means for supporting interdental gingival tissue; and
   securing means for securing the supporting means to an interimplant bone;
wherein the support means comprises a base; and
wherein the base comprises:
   a bottom surface with a left bottom edge, a right bottom edge, a front bottom edge and a rear bottom edge;
   a left side surface defined by the left bottom edge and a left curved edge connecting the endpoints of the left bottom edge, wherein a left side interior angle formed between the left side surface and the bottom surface is greater than about sixty degrees and less than about ninety degrees;
   a right side surface defined by the right bottom edge and a right curved edge connecting the endpoints of the right bottom edge, wherein a right side interior angle formed between the right side surface and the bottom surface is about equal to the left side interior angle; and
   a top surface defined by the front bottom edge, the rear bottom edge, the left curved edge and the right curved edge.

10. The apparatus of claim 9, wherein the base is characterized by dimensions comprising:
    a top width measured at a highest point of the base;
    a bottom width about three times the top width;
    a length about six times the top width; and
    a height about three times the top width.

11. The apparatus of claim 10, wherein the top width is to 0.5 millimeters, wherein the bottom width is about 1.5 millimeters, wherein the length is about 3 millimeters and wherein the height is about 1.5 millimeters.

12. An apparatus for simulating interdental papilla, comprising:
    support means for supporting interdental gingival tissue; and
    securing means for securing the supporting means to an interimplant bone
wherein the securing means comprises at least one stabilizing pin and wherein at least one stabilizing pin extends downward from the support means and wherein at least one stabilizing pin comprises a substantially triangular plane sharing an edge with a bottom surface of the support means.

13. An apparatus for simulating interdental papilla, comprising:
    a base sized to be positioned within an interdental embrasure and beneath at least a portion of the interdental gingival tissue; and
at least one stabilizing pin downwardly extending from the base for securing the base to an interimplant bone,
wherein the base comprises:
   a bottom surface with a left bottom edge, a right bottom edge, a front bottom edge and a rear bottom edge;
   a left side surface defined by the left bottom edge and a left curved edge connecting the endpoints of the left bottom edge, wherein a left side interior angle formed between the left side surface and the bottom surface is greater than about sixty degrees and less than about ninety degrees;
   a right side surface defined by the right bottom edge and a right curved edge connecting the endpoints of the right bottom edge, wherein a right side interior angle formed between the right side surface and the bottom surface is about equal to the left side interior angle; and
   a top surface defined by the front bottom edge, the rear bottom edge, the left curved edge and the right curved edge.

14. The apparatus of claim 13, wherein the at least one stabilizing pin further comprises a front stabilizing pin and a rear stabilizing pin.

15. The apparatus of claim 14, wherein at least one of the stabilizing pins has a hardness and sharpness sufficient for anchoring into the interimplant bone.

16. A papilla tack for simulating interdental papilla, comprising:
    a base sized to be positioned between osseointegrated dental implants, within an interdental embrasure and beneath at least a portion of the interdental gingival tissue, the base comprising:
       a bottom surface with a left bottom edge, a right bottom edge, a front bottom edge and a rear bottom edge;
       a left side surface defined by the left bottom edge and a left curved edge connecting the endpoints of the left bottom edge, wherein a left side interior angle formed between the left side surface and the bottom surface is greater than about sixty degrees and less than about ninety degrees;
       a right side surface defined by the right bottom edge and a right curved edge connecting the endpoints of the right bottom edge, wherein a right side interior angle formed between the right side surface and the bottom surface is about equal to the left side interior angle; and
       a top surface defined by the front bottom edge, the rear bottom edge, the left curved edge and the right curved edge;
    wherein the base is characterized by dimensions comprising:
       a top width measured at a highest point of the base;
       a bottom width about three times the top width;
       a length about six times the top width; and
       a height about three times the top width;
    a front stabilizing pin downwardly extending from the base for securing the base to an interimplant bone; and
    a rear stabilizing pin downwardly extending from the base for securing the base to an interimplant bone;
    wherein each of the front and rear stabilizing pins comprise a substantially triangular plane sharing an edge with the bottom surface; and
    wherein each of the front and rear stabilizing pins have a hardness and sharpness of a magnitude such that each of the front and rear stabilizing pins are adapted to be anchored into the interimplant bone.

17. The apparatus of claim 16, wherein the top width is about 0.5 millimeters, wherein the bottom width is about 1.5 millimeters, wherein the length is about 3 millimeters and wherein the height is about 1.5 millimeters.

18. Apparatus for simulating interdental papilla, comprising:
   a) generally trapezoidally shaped polyhedron configured means for supporting gingival tissue, comprising:
      i) a planar rectangular base;
      ii) a continuously curved convex surface extending between respective ends of the base and tapering from wider at junction with the ends of the base to narrower at a position equidistant therebetween;
      iii) planar surfaces extending between respective sides of the base and corresponding edges of the convex surface; and
   b) pins extending outwardly and perpendicularly from respective ends of the base for securing the supporting means to bone in the oral cavity.

* * * * *